United States Patent [19]
Korejwo

[11] Patent Number: 6,096,008
[45] Date of Patent: Aug. 1, 2000

[54] OPERATIONS SYSTEM

[76] Inventor: Richard Korejwo, Karmeliterweg 25, D-13465 Berlin, Germany

[21] Appl. No.: 09/065,830

[22] Filed: Apr. 24, 1998

[51] Int. Cl.[7] ..................................................... A61M 1/00
[52] U.S. Cl. ............................................. 604/151; 604/35
[58] Field of Search ................................. 604/67, 31, 35, 604/65, 131, 151, 156, 45, 36; 128/DIG. 12; 200/245, 250, 51.02

[56] References Cited

U.S. PATENT DOCUMENTS

| | | | |
|---|---|---|---|
| 5,098,387 | 3/1992 | Wiest et al. | 604/31 |
| 5,325,867 | 7/1994 | Skrabel et al. | 604/30 X |
| 5,718,668 | 2/1998 | Arnett et al. | 604/35 X |
| 5,772,635 | 6/1998 | Dastur et al. | 604/67 X |
| 5,810,765 | 9/1998 | Oda | 604/35 X |
| 5,836,909 | 11/1998 | Cosmescu | 604/35 |

FOREIGN PATENT DOCUMENTS

| | | |
|---|---|---|
| 34 05 403 | 8/1985 | Germany . |
| 39 33 856 | 5/1992 | Germany . |
| 195 25 926 | 11/1996 | Germany . |
| 195 29 017 | 1/1997 | Germany . |

*Primary Examiner*—Wynn Wood Coggins
*Assistant Examiner*—A. T. Nguyen
*Attorney, Agent, or Firm*—Nields, Lemack & Dingman

[57] ABSTRACT

Operation system with a gas and/or liquid pump, to which is connected at least one flexible-tubing line and which includes at least one control device controlling the flow-through quantity of the gas and/or the liquid in the flexible-tubing line, is proposed. In addition, an operator's control unit with actuating elements is provided, which is joined to the control device by means of a control line and with which the flow-through quantity can be adjusted. Control line (24) and actuating elements (16, 17) form at least two control channels independent of one another and the control device includes a memory, which stores a multiple number of control programs providing application-specific procedures, which can be selected on and off by a specific actuation pattern of actuating elements (16, 17). Prespecified actuation patterns of actuating elements (16, 17) are assigned to the control programs, by means of which the course of the application-specific procedure can be controlled.

13 Claims, 2 Drawing Sheets

FIG. I

OPERATIONS SYSTEM

BACKGROUND OF THE INVENTION

The invention proceeds from an operation system according to the preamble of the principal claim.

In surgical operations and interventions, particularly in minimally invasive surgery, laparoscopy, hysteroscopy and so forth, medical devices are used, particularly aspirating-flooding pumps, which have functions that must be controlled differently. Assistants are available to the surgeon for control of the devices, and these persons trigger or change the parameters of the functions of the devices, when instructed by the surgeon, by means of actuating elements, such as buttons, sliders or switches. However, since the use of additional personnel during an operation is cost-intensive, there is a tendency for the surgeon himself to control the functions of the one or more medical devices from the site of the operation.

A device is disclosed in DE 3,933,856 C2 for flooding and aspirating body cavities by means of a medical instrument with a pressure pump and an aspiration pump with connected flexible-tubing lines to body cavities for aspiration and flooding. The flexible-tubing lines are joined with a peristaltic pump. In addition, the device has a fluid-operated control line, which is connected on one side with the medical instrument and on the other side with a control device, which is a component of the peristaltic pump. The pressure in the control line is measured by a pressure sensor connected with an electronic evaluation device, whereby the pressurizing and aspirating pump is controlled dependent on pressure. The pressure in the control line can in turn be controlled by the surgeon by means of the control valve present on the medical instrument.

Such control of the function of aspiration and flooding of a peristaltic pump is very expensive and cumbersome.

DE 3,405,403 A1 describes a surgical aspirator arrangement, in which switching elements are provided directly on the aspirator handle, and the aspirator pump is actuated with these means and the pumping aspiration power can be increased or decreased thereby. The switching elements are connected to introduction lines, which are connected to the aspirator pump and are combined in a shielded cable.

A device for aspirating and flooding is also known from the non-prepublished DE 195-29,017 A1, which has a remote operation, whereby the remote operation has a transmission light conductor connected with a radiation source and a receiver light conductor connected with a radiation receiver, whose ends lie opposite one another in an actuation housing, whereby the light current can be varied between transmission light conductor and receiver light conductor, depending on an actuating element provided in the actuation housing and produces a variable electrical signal corresponding to the receiver. This signal is used for control of the pump.

SUMMARY OF THE INVENTION

The invention takes on the task of creating an operation system, with which a surgeon can control a multiple number of functions of the operation system during the surgical operation from the sterile region.

This task is resolved according to the invention by the characterizing features of the principal claim in combination with the preamble.

Due to the fact that the control line and the actuating elements of the operator's control unit to be operated by the surgeon form two control channels independent of one another and that the control device includes a memory, which stores a multiple number of control programs providing application-specific procedures, which can be selected on and off by a specific actuation pattern of the operating elements and that the actuation patterns of the actuating elements that are determined in advance are assigned to the control programs, and these patterns control the course of the application-specific procedure selected by the program in question, a means is made available to the surgeon, by means of which he can select and control a multiple number of different application-specific procedures during the operation from the sterile region, without needing another operating assistant present.

Advantageous further embodiments and improvements are possible by means of the measures indicated in the subclaims. Due to the fact that the control line has at least two light conductors transmitting radiation and receiving radiation, between which a transmission segment transmitting the radiation is formed each time, and that a control element that can be actuated by actuating elements of the operator's control unit is provided in the transmission segment, with which the light current or the radiation power of the transmitted light or radiation can be changed, a reliable means is made available for control. The configuration of the control line and the operator's control unit, whereby the latter has a plastic housing, makes possible the sterilizing of the control, so that application is possible in the sterilizing region. Due to the multiplicity of program selection, a broad application is possible and the operation system can be joined with other units or devices, such as a device for aspiration of fumes, a high-frequency generator device with appropriate control elements, an insufflator or a laser unit or the like, whereby the program that is turned on can be aligned accordingly and can be controlled by means of the actuating elements of the operator's control unit.

Examples of embodiment of the invention are shown in the drawing and will be explained in more detail in the following description. Here:

DETAILED DESCRIPTION OF THE INVENTION

Figure 1:
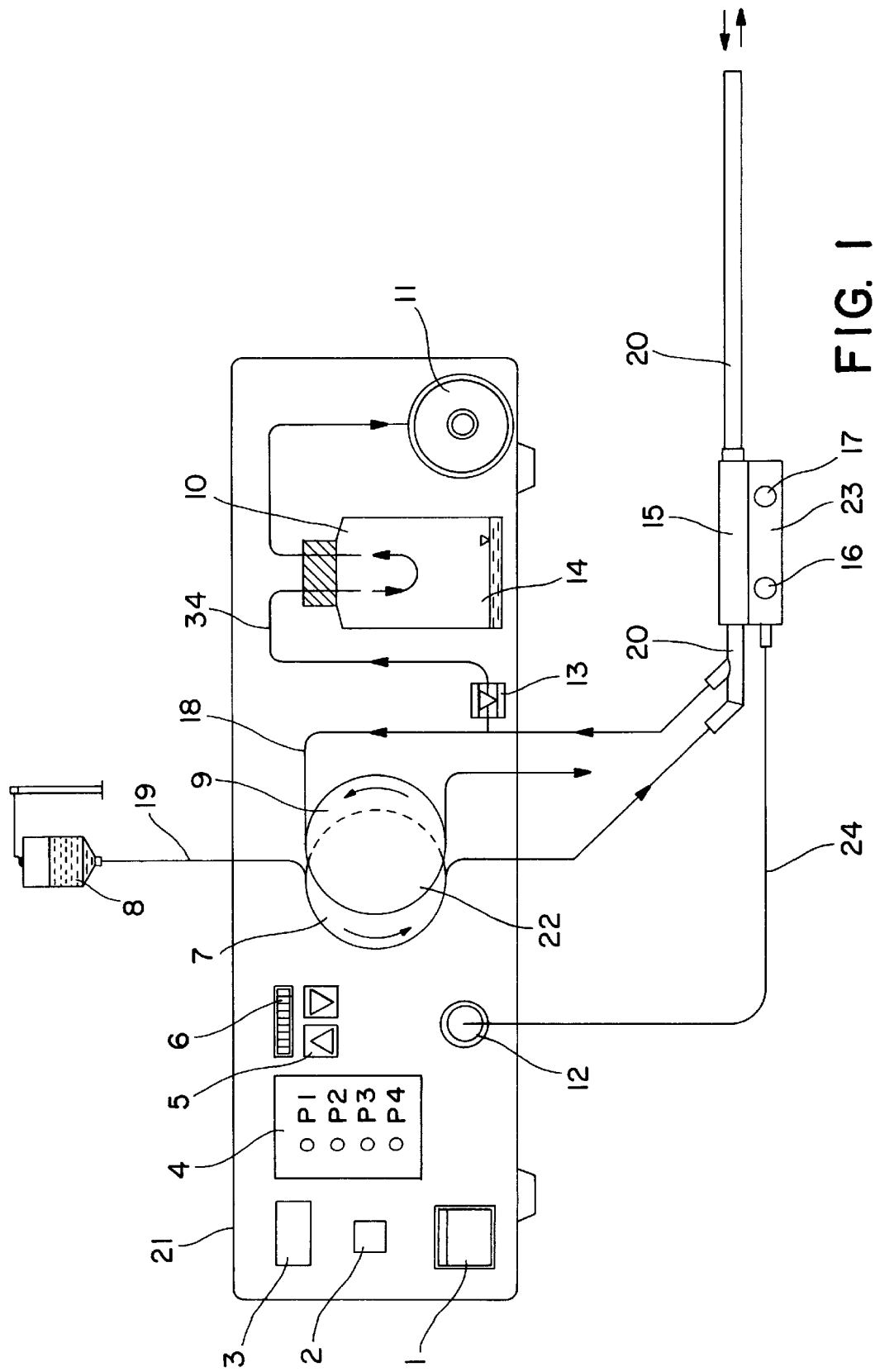
FIG. 1 shows a view onto the operation system of the invention.

Pump 22 shown in FIG. 1 is configured as an aspirating-flooding pump, and is used, for example, in microinvasive surgery for flooding and aspirating of body cavities. Pump 22 is a peristaltic pump, which has two roller wheels 7, 9 driven by motors, whereby flexible-tubing lines 18, 19 are guided over roller wheels 7, 9. Roller wheels 7, 9 are displaced relative to one another and shown purely schematically in the figures for better understanding; they or their axes, however, lie coaxially to one another. Flexible-tubing line 19 serving for flooding and driven by roller wheel 7 is joined with a supply container 8 for the flooding fluid, while flexible-tubing line 18 serving for aspirating and driven by roller wheel 9 is joined with a collecting container (not shown). Flexible-tubing lines 18, 19 open up into aspirating-flooding cannula 20, which is a component of a hand instrument 15. Cannula 20 is held by the surgeon by means of hand instrument 15 and placed at or in the body cavity.

The one or more motors receive their drive signals as control signals from a control device (not shown), which is taken up in housing 21 of pump 22, whereby the rpm values of roller wheels 7, 9 are controlled dependent on the control signals, whereby again the flow-through quantities desired during the aspirating or flooding process can be adjusted. This adjustment can be undertaken by the surgeon, for which operator's control unit 23 is provided, which has first and second operating buttons 16, 17 as actuating elements, which is joined by a control line 24 with the control device. Operator's control unit 23 is a component of hand instrument 15.

Figure 2:
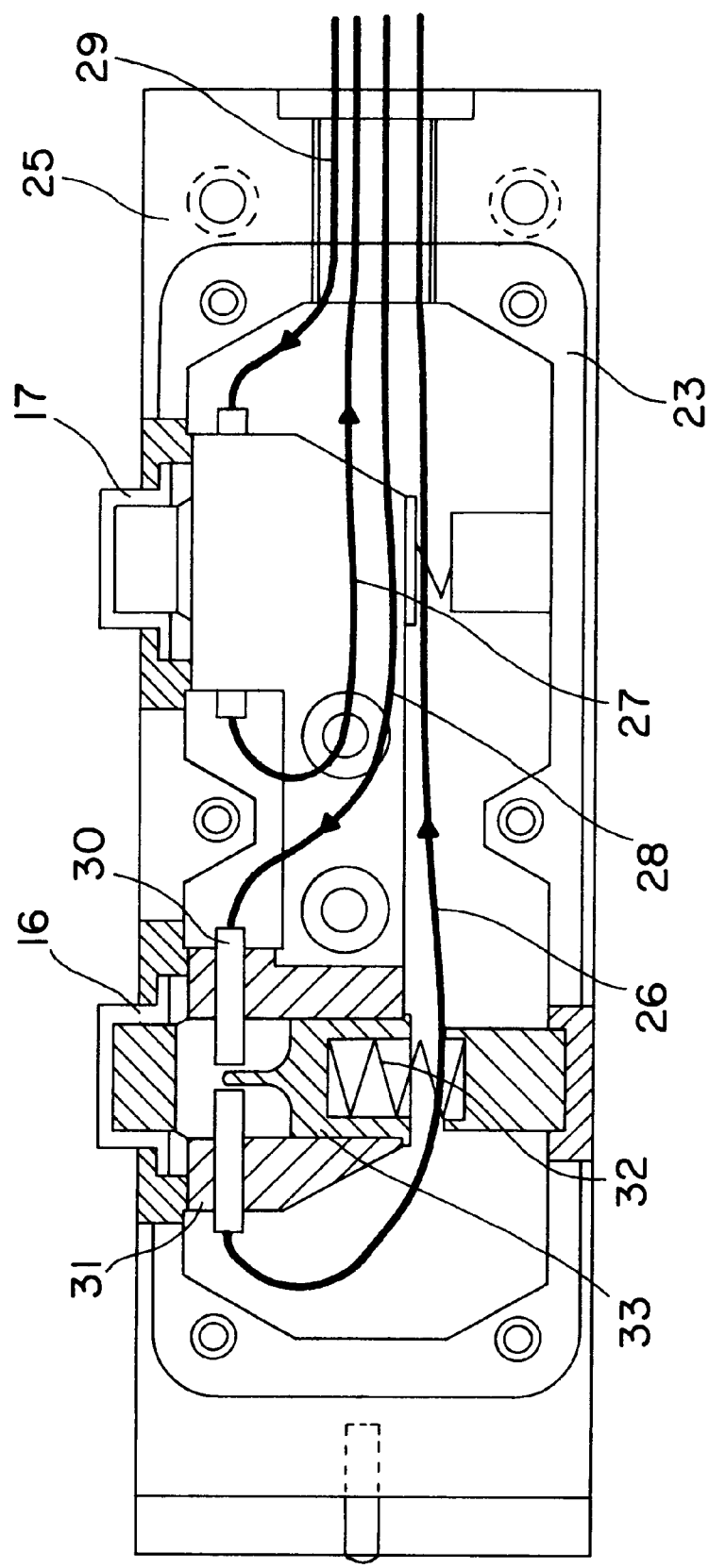
FIG. 2 shows a side view, partially cut away, of the operator's control unit according to the invention.

A section through operator's control unit 23 is shown in FIG. 2, in which operating buttons 16, 17 are taken up in a plastic housing 25, which can be sterilized. Control line 24 is formed in the present example of embodiment by four light-conducting cables, i.e., two transmitting light conductors 28, 29 as well as two receiving light conductors 26, 27 are provided, whereby transmitting light conductors 28, 29 are actively connected with at least one radiation source, for example, a light-emitting diode, and the receiving light conductors 26, 27 are each actively connected to a radiation receiver, for example, a phototransistor. Radiation source and radiation receiver are components of the control device.

The ends of light conductors 26 to 29 are taken up in a sleeve 30 attached in a holder 31 in such a way that one transmitting light conductor 28, 29 and one receiving light conductor 26, 27 stand opposite one another at a distance. A control element 33 guided in a spring-loaded manner engages in the gap between transmitting light conductors 28, 29 and receiving light conductors 26, 27, whereby this element can be varied in its position by pressure on buttons 16, 17 against the spring force in such a way that the radiation that is interrupted in the resting state of buttons 16, 17, which is dependent on the pressure force on the buttons, and is variable in its radiation power, is transmitted from transmitting light conductors 28, 29 to receiving light conductors 26, 27 and is guided onto the respective receiver, which transforms the radiation into the corresponding variable electrical signals, which are used by the control device for control of the motors of roller wheels 7, 9. Buttons 16, 17 and light conductors 26 to 29 joined with the control device by means of connection 12 form two control channels, which can further conduct signals independently of one another by means of buttons 16, 17.

Since the processes of pump 22 can be controlled not only by means of operator's control unit 23, operating elements are also provided on the pump itself, i.e., a power switch 1, a start/stop button 2, and a program button 3, and two adjusting buttons 5, for a continual adjustment of the flow-through quantities. In addition, a program selection field 4 formed as a display unit as well as a flow-through quantity indicator 6 in the form of a bar graph display are arranged in the front plate of housing 21. Operating elements and display units are joined with the control device.

An aspirating device for fumes, which has a fume aspirating line 34 branched off from aspirating line 18 is assigned to pump 22. It leads in and out of an intermediate tank 10 to a filter arrangement 11, which can be the component of an aspirating pump for fumes. A clamping valve 13, which is opened for the aspiration of fumes, is provided at the branch point of aspiration lines 18, 34.

A pressure monitoring system with integrated air-bubble detector, as is known from DE 195-25,926 C1, whose disclosure is also integrated herein, if necessary combined with an air-bubble discharge also known in and of itself, can be arranged in the flexible-tubing line 19 leading to operator's control unit 23.

The control device has a microprocessor with corresponding memories, which process the signals of operator's control unit 23 or the signals indicated by operating elements 1, 2, 3, 5. Various programs P1, P2, P3, P4, are provided for the different application-specific procedures, and these are stored in the memory of the microprocessor or microcomputer and they can be turned on and off by means of program button 2 on the pump or by means of operating buttons 16, 17 of operator's control unit 23. The course of the respective application-specific procedure as well as its parameters are controlled by the individual programs, depending on the type, the time duration, and/or the time sequence of actuating buttons 16, 17.

The following application-specific procedures are assigned to the programs in the example of embodiment.

Program 1 includes the normal aspirating-flooding function;

Program 2 supplies the possibility for flooding as needed with constant aspiration; program 3 offers simultaneous flooding and aspirating with desired power; and program 4 comprises an aspiration of fumes with spontaneous flooding.

The program selection is conducted as follows.

Both buttons 16, 17 of operator's control unit 23 are pressed and held, i.e., the maximum light current or the maximum radiation power is received by both receiving light conductors and the receivers supply the maximum electrical signals to the microprocessor, which selects the programs sequentially depending on the signals and controls program selection field 4 correspondingly, i.e., after approximately two seconds, the light-emitting diodes of field 4 begin to "migrate", i.e., they are cyclically controlled one after the other. At the moment when the light-emitting diode is illuminated at the desired program, both buttons 16, 17 must be released; in this case, the signal level changes from maximum to minimum and the microprocessor terminates its cyclical inquiry and the desired program P1 to P4 is selected. The program selection may be turned on and off of course, by program selection button 3 and start/stop button 2.

If program 1, i.e., the normal aspirating-flooding function is selected, the signals initiated by means of buttons 16, 17 are converted by the microprocessor such that the rpm of the respective roller wheel 7, 8 and thus the aspirating or flooding power, i.e., the respective flow-through quantity of flexible-tubing lines 18, 19 is proportional to the exercised pressure force on buttons 16, 17, by which control element 33 is removed proportionally from the gap. A releasing of either button 16, 17 causes an immediate stopping of roller wheels 7, 8.

If program 2 is selected, i.e., flooding with constant aspirating, the second button 17 is pressed. Thus the magnitude of the flow-through quantity for aspirating can be read off the flow-through quantity indicator 6. Of course, another digital or analog display can be provided. If the rpm of roller wheel 9, as a response to the pressure force on the second button 17, corresponds to the desired value, the latter is established by a brief pressing of first button 16. After releasing buttons 16, 17, pump 22 aspirates at constant power. Flooding is actuated by actuating first button 16, whereby the flooding power (rpm) is proportional to the pressure force exercised. The continuous aspirating process is terminated by briefly pressing second button 17.

In the case of program 3 for simultaneous flooding and aspirating with desired power, both roller wheels 7, 9 rotate with the same rpm or speed if second button 17 on operator's control unit 23 is pressed. If this corresponds to the desired value, based on the pressure force introduced, it is fixed with a short pressing (click) on first button 16. The process is stopped with a click on second button 17.

Program 4 makes possible the aspiration of fumes. When this program is selected, the microprocessor gives a control command to clamping valve 13, which opens. Second button 17 on operator's control unit 23 is pressed, whereby the magnitude of aspirating power is adjusted proportional to the pressing force, which is shown on bar graph display 6. If the desired step on bar graph display 6 is reached, the second button 17 is released and the performance of fume aspiration is preselected. By tapping first button 16, aspiration is activated. Thus, the fumes are guided from the body cavity into intermediate container 10, whereby entrained aspirated liquid 14 also settles in container 10. Filter 11 filters the gas further conducted from intermediate container 10. A repeated short actuation of first button 16 interrupts the fume aspirating process.

In the case of the example of embodiment shown, the aspirating and flooding lines or the aspirating-flooding channels are arranged directly next to one another and are taken up in hand instrument 15. However, they may be guided also on separate paths to the one or more body cavities and attached there, so that the surgeon holds only operator's control unit 23 in his hand.

An aspirating-flooding pump is an essential component of a surgical operation, which can barely be dispensed with in an operation system. It is thus meaningful to assign to the pump other devices of the operation system, such as an insufflator, i.e., a $CO_2$-gas pump for insufflating body cavities, a HF unit for introducing high-frequency energy into the regions of the body cavities, or a laser unit or the like. In this case, the devices are connected to the pump by means of a serial interface, which is joined with the control device, and additional and/or other programs are provided, which are stored in the microprocessor or the control device and are assigned to other application-specific procedures. However, it is also conceivable that only one insufflator is controlled with several programs.

In addition, more than two control channels, i.e., additional buttons on the operator's control with additional light conductors may be provided.

What is claimed is:

1. Operation system having a gas and/or liquid pump, to which is connected at least one flexible-tubing line, said system further comprising:
   at least one control device controlling the flow-through quantity of the gas and/or the liquid in said flexible-tubing line,
   an operator's control unit with actuating elements, which is connected to said control device by means of a control line and with which the flow-through quantity can be adjusted,
   said control line (24) and actuating elements (16, 17) together forming at least two control channels independent of one another, wherein one control channel has radiation-conducting cables for transmitting light radiation and receiving light radiation,
   said control device containing memory means for storing a multiple number of application-specific procedures of pregiven control programs, which can be selected on or off by a specific actuation pattern of said actuating elements (16, 17) and that actuation patterns of said actuating elements (16, 17), which are determined in advance, are assigned to the control programs, and these patterns control the course of the application-specific procedure, said actuating elements being effectively connected with a control element (33) which controls the magnitude of the transmitted light radiation depending on the actuation of said actuating elements.

2. Operation system according to claim 1, wherein said control element (33) of said operator's control unit (23), which controls the magnitude of the radiation transmitted between transmitting and receiving radiation-conducting cables, is formed as a blocking device.

3. Operation system according to claim 1, wherein the gas and/or liquid pump is an aspirating-flooding pump (22) configured as a peristaltic pump.

4. Operation system according to claim 3, wherein the gas and/or liquid pump has roller wheels driven by at least one motor, said roller wheels guiding said at least one flexible tubing line, said roller wheels each having a drive shaft formed coaxially to one another.

5. Operation system according to claim 1, wherein the radiation-conducting cables (28, 29) that transmit light radiation are connected to a light radiation transmitter and the light radiation-conducting cables (26, 27) receiving light radiation are connected to a light radiation receiver.

6. Operation system according to claim 1, wherein said gas and/or liquid pump (22) further comprises a fume aspiration device (10, 11, 34), whereby said at least one flexible-tubing line (18) configured for aspiration is connected by means of an aspiration line (34) for fumes with fume aspiration device (10, 11), and that a control program controls the aspiration of fumes.

7. Operation system according to claim 6, further comprising a clamping valve (13) in said fume aspiration line (34), said valve being opened when the control program for the aspiration of fumes is selected "on".

8. Operation system according to claim 1, wherein said pump (22) further comprises a first display unit (4) for display of the selected control program.

9. Operation system according to claim 8, wherein said pump (22) further comprises a second display unit (6) for indicating the magnitude of the flow-through quantity.

10. Operation system according to claim 1 or 8, wherein when said actuating elements (16, 17) are actuated for turning "off" one of said pregiven control programs, said control device controls said program and said first display unit is cyclically controlled, and wherein at the point in time when said actuating elements (16, 17) are released, one of said pregiven control programs that was directly turned on is turned-off.

11. Operation system according to claim 1, wherein said control device further comprises a microprocessor.

12. Operation system according to claim 1, further comprising at least one other device of the operation system, whose parameter can be controlled by means of a control program, is in communication with said gas and/or liquid pump (22).

13. Operation system according to claim 12, wherein said control device of pump (22) further comprises a serial interface, by means of which said at least one other device is connected.

* * * * *